United States Patent [19]

Brunetta et al.

[11] Patent Number: 5,368,847
[45] Date of Patent: Nov. 29, 1994

[54] STABLE EMULSIONS OF PERFLUOROPOLYETHERS AND FAT SUBSTANCES AND PROCESS FOR PREPARING THEM

[75] Inventors: Fabio Brunetta, Cornuda; Giovanni Pantini, Milan, both of Italy

[73] Assignee: Ausimont S.p.A., Milan, Italy

[21] Appl. No.: 809,761

[22] Filed: Dec. 18, 1991

[30] Foreign Application Priority Data

Dec. 18, 1990 [IT] Italy .................. 22415 A/90

[51] Int. Cl.$^5$ .................. A61K 7/02; A61K 7/027
[52] U.S. Cl. .................. 424/61; 424/401; 424/63; 424/64; 424/59; 514/844; 514/937; 252/DIG. 5
[58] Field of Search .................. 424/401, 63, 59, 64, 424/78.03; 514/844, 937; 252/DIG. 5

[56] References Cited

U.S. PATENT DOCUMENTS 4,803,067  2/1989  Brunetta et al. .................. 424/63
5,093,023  3/1992  Pantini et al. .................. 252/174.23

FOREIGN PATENT DOCUMENTS 0196904  3/1986  European Pat. Off. .
0390206  3/1990  European Pat. Off. .

Primary Examiner—Thurman K. Page
Assistant Examiner—Amy Hulina
Attorney, Agent, or Firm—Bryan Cave

[57] ABSTRACT

The invention relates to stable emulsions of perfluoropolyethers having perfluoroalkyl end groups and of fat substances, consisting of:
 one or more perfluoropolyethers having perfluoroalkyl end groups: 1–50% by weight,
 one or more polyhydroxylated compounds selected from glycerol and polyalcohols other than glycerol and saccharides, containing at least three hydroxylic groups, said compounds being dissolved in water or in a hydrophilic solvent when they are solid: 10–95% by weight, including water and the hydrophilic solvent, if any,
 one or more fat substances having a melting temperature not higher than 100° C.: 10–80% by weight,
 one or more emulsifiers: 0.1–10% by weight.

These emulsions are utilized, in particular, in cosmetology and dermatology.

13 Claims, No Drawings

STABLE EMULSIONS OF PERFLUOROPOLYETHERS AND FAT SUBSTANCES AND PROCESS FOR PREPARING THEM

The present invention relates to stable emulsions of perfluoropolyethers having perfluoroalkyl end groups and of fat substances.

It is known that said perfluoropolyethers exhibit a very high hydrophobicity and lipophobicity, wherefore it was possible to prepare stable aqueous emulsions thereof only by by means of particular combinations of components of the same emulsions.

U.S. Pat. No. 4,803,067 discloses stable emulsions of perfluoropolyethers having perfluoroalkyl end groups in oil/water emulsions or water/oil emulsions obtained by using emulsifiers. These emulsions are utilized, in particular, in lotions and creams for cosmetology and dermatology, in consideration of the excellent properties of said perfluoropolyethers in said applications, due to the particular formation, on the skin, of a water-repellent, oxygen-permeable and carbon dioxide-permeable protective film, which permits the normal skin respiration.

European Patent Application No. 390.206 describes stable emulsions of perfluoropolyethers having perfluoroalkyl end groups in glycerol or other polyhydroxylated compounds, prepared by using emulsifiers. In the preparation of cosmetic or dermatological products, the above said emulsions are added to basic formulations containing the other components.

So far it was not possible to obtain stable emulsions of perfluoropolyethers with fat substances, although the need for such emulsions of anhydrous or substantially anhydrous nature was strongly felt in the cosmetic and dermatological sectors or in industrial appliances, wherein said anhydrous or substantially anhydrous emulsions would have permitted to preserve the hydrophobic nature of the anhydrous products whereinto they would have been introduced.

It has now been found that it is possible to obtain stable emulsions of perfluoropolyethers having perfluoroalkyl end groups (hereinafter briefly referred to as perfluoropolyethers) and fat substances if one or more fat substances in the liquid state is or are added, under stirring, to an emulsion of perfluoropolyether in glycerol or other polyhydroxylated compounds in the presence of a surfactant which is soluble in glycerol or in the other polyhydroxylated compounds.

The existence of said stable emulsions of perfluoropolyethers and fat substances in glycerol or other polyhydroxylated compounds is very surprising since it is not possible to emulsify a fat substance in glycerol or in another polyhydroxylated compound and it is not possible to emulsify a perfluoropolyether in a fat substance. It has surprisingly been found that the presence of a perfluoropolyether in emulsion in glycerol or other polyhydroxylated compounds makes it possible to emulsify the fat substance in the perfluoropoly-ether-glycerol system or in the perfluoropolyether-other polyhydroxylated compounds system.

Thus, it is an object of the present invention to provide stable, anhydrous or substantially anhydrous emulsions of perfluoropolyethers and fat substances.

Another object is to provide a process for preparing such emulsions.

The former object is achieved by the stable emulsions of perfluoropolyethers having perfluoroalkyl end groups and of fat substances, conforming to the present invention, which are composed of:
- one or more perfluoropolyethers having perfluoroalkyl end groups: 1–50% by weight,
- one or more polyhydroxylated compounds selected from glycerol and the polyalcohols other than glycerol and the saccharides, containing at least three hydroxylic groups, said compounds being dissolved in water or in a hydrophilic solvent when they are solid: 10–95% by weight, including water and hydrophilic solvent, if any,
- one or more fat substances having a melting temperature not higher than 100° C.: 10–80% by weight,
- one or more emulsifiers: 0.1–10% by weight.

By the term fat substance it is meant:
1) a liquid product (oil) insoluble in water and in the polyhydroxylated compounds as defined hereinabove, and
2) a product which is solid at room temperature (fat), is insoluble in water and in the polyhydroxylated compounds and has a melting temperature not exceeding 100° C.

The perfluoropolyethers having perfluoroalkyl end groups, i.e. free from functional groups, are well-known compounds, which are described, along with their method of preparation, in several documents, among which British patent 1,104,482, U.S. Pat. Nos. 3,242,218; 3,665,041; 3,715,378; 4,523,039; European patent applications 148,482; 151,877 and 191,490 and international patent applications WO 87/00538 and WO 87/02992. Several perfluoropolyethers are available on the market under the trademarks Fomblin®, Galden®, Krytox® and Demnum®.

Suitable perfluoropolyethers are the ones characterized by the presence of one or more repeating perfluorooxyalkylene units:

a) $(CF_2-CF_2O)$
b) $(CF_2O)$
c) $(C_3F_6O)$, simplified formula for

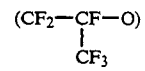

d) $(CF_2O-CF_2-CF_2O)$
e) $(CF_2-CF_2-CF_2O)$
f) $(CFO)CF_3$

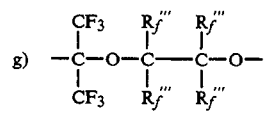

where the $R_f'''$ groups, like or unlike each other, are a fluorine atom or a perfluoroalkyl group preferably containing 1 to 3 carbon atoms.

Preferably the perfluoropolyethers suitable for the present invention exhibit the following individual perfluoro-oxyalkylene units or the following combinations of perfluoro-oxyalkylene units:

I) $(CF_2-CF_2O)$ and $(CF_2O)$, these units being statistically distributed along the perfluoropolyether chain; or

II)

$$(CF_2-CFO)$$
$$|$$
$$CF_3$$

and (CFXO), where X is F or $CF_3$, said units being statistically distributed along the chain; or

III) ($CF_2$—$CF_2O$), $$(CF_2-CFO)$$
$$|$$
$$CF_3$$

and (CFXO), wherein X is F or $CF_3$, said units being statistically distributed along the chain; or

IV)

$$(CF-CF_2O);$$
$$|$$
$$CF_3$$

or
V) ($CF_2$—$CF_2$—$CF_2O$); or
VI) ($CF_2$—$CF_2O$); or

VII)
$$\begin{array}{ccc} CF_3 & R_f''' & R_f''' \\ | & | & | \\ -C-O-C-\!\!-\!\!-C-O- \\ | & | & | \\ CF_3 & R_f''' & R_f''' \end{array}$$

where the $R_f'''$ groups, like or unlike each other, are a fluorine atom or a perfluoroalkyl group preferably containing 1 to 3 carbon atoms; or

VIII) ($CF_2O$—$CF_2$—$CF_2O$)

Suitable are also the perfluoropolyethers containing perfluorooxyethane rings $$\begin{array}{cc} T & B \\ | & | \\ -C-\!\!-\!\!-C- \\ | & | \\ CF-O \\ | \\ R \end{array} \quad \text{or} \quad \begin{array}{cc} O-\!\!-\!\!-CF-A \\ | & | \\ -C-\!\!-\!\!-C- \\ | & | \\ CF_2-CF_2 \end{array}$$

wherein T, A, B and R, like or different from one another, are perfluorooxyalkyl, perfluoropolyoxyalkyl or perfluoroalkyl radicals preferably containing 1 to 6 carbon atoms.

Examples of suitable perfluoropolyethers having repeating perfluorooxyalkylene units are the ones belonging to the following classes:

A)

$$R_f-O-(C_3F_6O)_a(CF-O)_b(CF_2O)_c-R_f'$$
$$|$$
$$CF_3$$

where: $R_f$ and $R'_f$, like or unlike each other, are selected from the group consisting of $CF_3$, $C_2F_5$ and $C_3F_7$; units $C_3F_6O$ (oxytrifluoromethyltrifluoroethylene), $$CF-O$$
$$|$$
$$CF_3$$

and $CF_2O$ are statistically distributed along the chain; a is an integer; b and c are integers or zero; when the sum (b+c) is other than zero, the $$\frac{a}{b+c}$$

ratio ranges from 5 to 40;

B) $CF_3O$—$(C_2F_4O)_d(CF_2O)_e$—$CF_3$ where units $C_2F_4O$ and $CF_2O$ are statistically distributed along the chain; d and e are integers; the d/e ratio varies from 0.3 to 5;

C) $CF_3O$—$(C_3F_6O)_f(C_2F_4O)_g$—$(CFXO)_h$—$CF_3$ where units $C_3F_6O$, $C_2F_4O$ and CFXO are statistically distributed along the chain; X is F or $CF_3$; f, g and h are integers; the $$\frac{f}{g+h}$$

ratio ranges from 1 to 50, and the $$\frac{g}{h}$$

ratio ranges from 1 to 10;

D) $R_\delta^3O$—$(CF_2CF_2CF_2O)_jR_\delta^4$ where $R_\delta^3$ and $R_\delta^4$, like or different from each other, are —$CF_3$ or —$C_2F_5$ and j is an integer.

The perfluoropolyethers suited to be used in the present invention have generally a number average molecular weight ranging from 500 to 20,000 and, more commonly, from 1,000 to 10,000.

The polyhydroxylated compounds suited to the present invention are described more in detail in the cited European patent application 390,206 in the name of the same Applicant, which is incorporated in the specification of the present invention as a reference.

When the polyhydroxylated compound is solid, it is dissolved in water or in a hydrophilic solvent. It is advisable to use the minimum amount of water or of hydrophilic solvent which is necessary to dissolve the compound.

Suitable hydrophilic solvents are, for example, glycols, glycerol, lower alcohols, ethereal solvents and diglymes, also admixed with water.

However, water is usually utilized as a solvent. Suitable are the concentrated aqueous solutions (syrups) of polyalcohols and saccharides, which are commercially available.

Usually the concentration of the solutions ranges from 50% to 80% by weight.

Best preferred polyhydroxylated compounds are glycerine, diglycerol, triglycerine and tetraglycerine.

The oils and the fats according to the present invention can be of vegetable, animal, hydrocarbon or synthetic nature. They are in particular fatty alcohols, acids, esters and amides, silicone oils and hydrocarbon oils and fats.

The emulsifier shall be soluble in the polyhydroxylated compound. Among the suitable emulsifiers, the following ones can be cited as examples:
sodium laurylsulphate,
sulpnosucciante (sulphosuccinic hemiester),
coco amphocarboxyglycinate,
potassium cetylphosphate,
sodium alkyl-polyoxyethylene-ether carboxylate,
benzalconium chloride,
alkylamidopropylbetaine,
coco amidopropylbetaine.

The emulsions according to the present invention have preferably the following composition:
perfluoropolyether or perfluoropolyethers: 5–25% by weight;
one or more polyhydroxylated compounds: 10–59% by weight;
fat substance or substances: 35–80% by weight;
emulsifier or emulsifiers: 0.3–3% by weight.

The most preferred emulsions contain from 10 to 40% by weight of polyhydroxylated compound.

Commonly, the emulsions contain only one perfluoropolyether and only one polyhydroxylated compound.

Depending on the nature and proportion of the components, the emulsions of the present invention exhibit a very wide viscosity range, which makes them suitable for a broad applicative field. The least viscous emulsions have, for example, a viscosity of 2,000 cps (centipoises) at 25° C., while the most viscous emulsions have, for example, a viscosity of 1,000,000 cps or above.

The viscosity increases with the concentration of the fat substances and of the perfluoropolyethers and when use is made of more viscous polyhydroxylated compounds.

At equal concentration, also the nature of the fat substances influences the viscosity.

The viscosity of the emulsions can be lowered, if so desired, by addition of water or of alcohols. Suitable alcohols are, for example, alkyl alcohols having 1 to 4 carbon atoms, and ethylene glycols containing 2 to 4 carbon atoms.

The addition of water or alcohol tends to lower the stability of the emulsions, wherefore it is not advisable to add more than about 20% thereof, calculated on the total weight of the emulsion.

The minimum added amount of water or alcohol is, for example, equal to 1%. If water or alcohol is added, the percent amount of the other components, of course, is reduced, although maintaining unaltered their reciprocal proportions.

The water- or alcohol-containing emulsions are useful in those applications in which a low or relatively low viscosity without a high hydrophobicity is desired.

According to the present invention, stable emulsions are considered the ones, which do not give rise to phase separation phenomena after centrifugation at 4,000 rpm for a time of 30 minutes and a subsequent treatment in oven at 50° C. for a week.

The emulsions according to the present invention can be prepared as follows: to an emulsion of one or more perfluoropolyethers in one or more polyhydroxylated compounds containing one or more emulsifiers which are soluble in said polyhydroxylated compounds (such emulsion will be briefly referred to as "pre-emulsion") there are added, under stirring, one or more fat substances in the liquid state.

The pre-emulsion is at a temperature, which is not critical; in most cases it is at room temperature.

When the fat substance is solid at room temperature, it is added to the pre-emulsion in the molten state or dissolved, in particular, in a liquid fat substance conforming to the present invention, preferably a hydrocarbon oil, while heating, if necessary, in order to favour the dissolution.

When the fat substance is added at a temperature above the room temperature, it is advisable to preheat the pre-emulsion to a temperature next or equal to the temperature of the fat substance.

The preparation of the pre-emulsions is described in detail in European patent application 390,206 already cited herein.

Such emulsions are preparable by adding the perfluoropolyether or perfluoropolyethers, under stirring, to a solution of one or more emulsifiers in one or more polyhydroxylated compounds.

At the end of the addition it is advisable to go on stirring at a lower speed, for example for 30–120 minutes, in order to obtain the best homogenization.

It is assumed that she outer phase of the emulsions according to the present invention consists of the polyhydroxylated compound or compounds, while the perfluoropolyether or perfluoropolyethers and the fat substance or substances constitute inner dispersed phases. In fact, these emulsions are dilutable with glycerol and with water (without having recourse to mechanical stirring), but are not dilutable with perfluoropolyethers and fat substances (unless mechanical stirring is utilized). Also the fact that the viscosity increases as the content of perfluoropolyethers or of fat substances increases, indicates that these two types of components form the inner phases.

The emulsions of the present invention have a wide field of uses in cosmetology and dermatology and in the industrial sector.

The introduction of liposoluble substances into the oily phase (such as, for example, vitamins or solar filters) or of glycerol-soluble substances permits to functionalize the cosmetic and dermatological preparations.

Among the cosmetic applications there are to be cited for example: barrier creams, sun-preparations, lip-ointments and anhydrous cosmetics, such as lipsticks and sticks.

Among the dermatological applications there are to be cited, for example, the skin protective preparations and the medicament-slow-release preparations.

Among the industrial applications there are to be cited the lubrication and the water-repellent treatments of textiles and leather.

The anhydrous nature of the emulsions, or in any case, the presence therein of little water amounts, makes biologically more stable the cosmetic and dermatological products prepared with said emulsions. In fact, said products do not require, usually, the presence of preservatives. Also the anhydrous nature of the emulsions secures a higher persistence of said products on the skin. A further advantage in the same applicative fields consists in the fact that the emulsions according to the present invention require the presence of lesser amounts of surfactant than the ones which are contained in the emulsions of perfluoropolyethers in water/oil or oil/water emulsions described in the above-cited U.S. Pat. No. 4,803,067.

The following examples are given merely for illustrative purposes and should not be construed to be a limitation of the scope of the present invention.

Examples 1 to 33 illustrate various emulsions conforming to the present invention and the modalities for preparing them. All the compositions are indicated in % by weight.

The stability test is the one previously described.

The utilized perfluoropolyethers have the structure and the characteristics indicated hereinbelow:
Fomblin HC/25

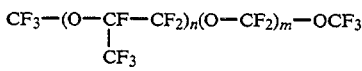

n/m=20 to 40 M.W. (number average molecular weight)=3,200.

Galden D03 the same formula as the preceding product n/m=20 to 40 M.W.=870

Fomblin HC/R the same formula as the preceding product n/m=20 to 40 M.W.=6,600

Demnum S-65 $F(CF_2-CF_2-CF_2O)_nCF_2CF_3$ M.W.=4,500

Fomblin Z25 $CF_3-(OCF_2CF_2)_p(OCF_2)_q-OCF_3$ p/q=0.6 to 0.7 M.W.=9,400

EXAMPLE 1

| Fomblin HC/25 | 59% |
| --- | --- |
| Glycerol | 29% |
| Texapon N/40* | 2% |
| Vaseline oil (density: 0.83) | 10% |

*sodium lauryl sulphate (solution at 28%) produced by Henkel.

Into the pre-emulsion of Fomblin HC/25, glycerol and Texapon N/40, the vaseline oil was added at room temperature, while stirring by means of a Silverson L/2R turbo-emulsifier at 5,000–6,000 rpm.

Unless otherwise specified, the emulsions illustrated in the following examples were prepared according to the same procedure.

The emulsion was stable. Its viscosity, as well as the one of the emulsions of the subsequent examples, was determined by means of a Brookfield digital eight-speed viscosimeter, model RTV-II, following the manufacturer's rules.

Viscosity: 36,600 cps (centipoises) at 25° C. (5 r.p.m., impeller 29).

EXAMPLE 2

| Fomblin HC/25 | 29% |
| --- | --- |
| Glycerol | 59% |
| Texapon N/40 | 2% |
| Vaseline oil | 10% |

Viscosity: 2,000 cps (5 rpm, impeller 29) at 25° C. Stable emulsion.

EXAMPLE 3

| Fomblin HC/25 | 20% |
| --- | --- |
| Glycerol | 39% |
| Texapon N/40 | 2% |
| Vaseline oil | 39% |

Viscosity: 50,000 cps (5 rpm, impeller 29) at 25° C. Stable emulsion.

EXAMPLE 4

| Fomblin HC/25 | 15% |
| --- | --- |
| Glycerol | 29% |
| Texapon N/40 | 2% |
| Vaseline oil | 54% |

Viscosity: 950,000 cps (1 rpm, impeller 29) at 25° C. Stable emulsion.

EXAMPLE 5

| Fomblin HC/25 | 10% |
| --- | --- |
| Glycerol | 59% |
| Texapon N/40 | 2% |
| Vaseline oil | 29% |

Viscosity: 3,100 cps (5 rpm, impeller 29) at 25° C. Stable emulsion.

EXAMPLE 6

| Fomblin HC/25 | 20% |
| --- | --- |
| Glycerol | 39% |
| Texapon N/40 | 2% |
| Silicone oil (350 cps) | 39% |

Stable emulsion.

EXAMPLE 7

| Fomblin HC/25 | 20% |
| --- | --- |
| Glycerol | 39% |
| Texapon N/40 | 2% |

Mixture of 50% of silicone oil and 50% of vaseline oil 39% Stable emulsion.

EXAMPLE 8

| Fomblin HC/25 | 20% |
| --- | --- |
| Glycerol | 39% |
| Texapon N/40 | 2% |
| Abil K4 (volatile silicone) | 39% |

Stable emulsion.

EXAMPLE 9

| Fomblin HC/25 | 20% |
| --- | --- |
| Glycerol | 39% |
| Texapon N/40 | 2% |
| Wheat germ oil | 39% |

Stable emulsion.

EXAMPLE 10

| Fomblin HC/25 | 20% |
| --- | --- |
| Glycerol | 39% |
| Texapon N/40 | 2% |
| Jojoba oil | 39% |

Stable emulsion.

EXAMPLE 11

| Fomblin HC/25 | 20% |
| --- | --- |
| Glycerol | 39% |
| Texapon N/40 | 2% |
| Eutanol G (2-octyl-dodecanol) produced by Henkel | 39% |

Stable emulsion.

EXAMPLE 12

| | |
|---|---|
| Fomblin HC/25 | 20% |
| Glycerol | 39% |
| Texapon N/40 | 2% |
| Mirytol (triglyceride of the capric and caproic acids) produced by Henkel | 39% |

Stable emulsion.

EXAMPLE 13

| | |
|---|---|
| Fomblin HC/25 | 20% |
| Glycerol | 39% |
| Texapon N/40 | 2% |
| Octyl stearate (Cetiol 868 produced by Henkel) | 39% |

Stable emulsion.

EXAMPLE 14

| | |
|---|---|
| Fomblin HC/25 | 20% |
| Glycerol | 39% |
| Texapon N/40 | 2% |
| Olive oil | 39% |

Stable emulsion.

EXAMPLE 15

| | |
|---|---|
| Fomblin HC/25 | 20% |
| Glycerol | 39% |
| Texapon N/40 | 2% |
| Paraffin C10/C13 | 39% |

Stable emulsion.

EXAMPLE 16

| | |
|---|---|
| Fomblin HC/25 | 20% |
| Glycerol | 39% |
| Texapon N/40 | 2% |
| Ropy vaseline | 39% |

The ropy vaseline was introduced in the molten state at a temperature of about 55° C. into the pre-emulsion preheated to 45° C. Stable emulsion.

EXAMPLE 17

| | |
|---|---|
| Fomblin HC/25 | 20% |
| Glycerol | 39% |
| Texapon N/40 | 2% |
| Ropy vaseline | 13% |
| Paraffin C10/C13 | 26% |

The ropy vaseline and the paraffin were premixed before being introduced into the pre-emulsion. Stable emulsion.

EXAMPLE 18

| | |
|---|---|
| Fomblin HC/25 | 20% |
| Glycerol | 39% |
| Texapon N/40 | 2% |
| Castor-oil | 39% |

Stable emulsion.

EXAMPLE 19

| | |
|---|---|
| Fomblin HC/25 | 20% |
| Glycerol | 39% |
| Texapon N/40 | 2% |
| Linseed-oil | 39% |

Stable emulsion.

EXAMPLE 20

| | |
|---|---|
| Fomblin HC/25 | 14% |
| Glycerol | 27% |
| Texapon N/40 | 2% |
| Vaseline oil | 52% |
| Water | 5% |

Water was added last. Stable emulsion. Viscosity: 37,500 cps at 25° C. (5 rpm, impeller 21).

EXAMPLE 21

| | |
|---|---|
| Fomblin HC/25 | 13% |
| Glycerol | 27% |
| Texapon N/40 | 2% |
| Vaseline oil | 43% |
| Water | 10% |

Stable emulsion. Viscosity: 7,000 cps at 25° C. (15 rpm, impeller 21).

EXAMPLE 22

| | |
|---|---|
| Fomblin HC/25 | 12% |
| Glycerol | 23% |
| Texapon N/40 | 2% |
| Vaseline oil | 43% |
| Water | 20% |

Stable emulsion.

EXAMPLE 23

| | |
|---|---|
| Galden DO3 | 20% |
| Glycerol | 39% |
| Texapon N/40 | 2% |
| Vaseline oil | 39% |

Stable emulsion.

EXAMPLE 24

| | |
|---|---|
| Fomblin HC/R | 20% |
| Glycerol | 39% |
| Texapon N/40 | 2% |
| Vaseline oil | 39% |

Stable emulsion.

EXAMPLE 25

| | |
|---|---|
| Demnum S/65 | 20% |

-continued

| | |
|---|---|
| Glycerol | 39% |
| Texapon N/40 | 2% |
| Vaseline oil | 39% |

Stable emulsion.

EXAMPLE 26

| | |
|---|---|
| Fomblin Z 25 | 20% |
| Glycerol | 39% |
| Texapon N/40 | 2% |
| Vaseline oil | 39% |

Stable emulsion.

EXAMPLE 27

| | |
|---|---|
| Fomblin HC/25 | 20% |
| Glycerol | 39% |
| Coco amidopropylbetaine | 2% |
| Vaseline oil | 39% |

Stable emulsion.

EXAMPLE 28

| | |
|---|---|
| Fomblin HC/25 | 20% |
| Glycerol | 39% |
| Benzalconium chloride (solution at 50% in water) | 2% |
| Vaseline oil | 39% |

Stable emulsion.

EXAMPLE 29

| | |
|---|---|
| Fomblin HC/25 | 20% |
| Diglycerol | 39% |
| Texapon N/40 | 2% |
| Vaseline oil | 39% |

Highly viscous, stable emulsion. Viscosity: 1,000,000 cps (5 rpm, impeller 29) at 25° C.

EXAMPLE 30

| | |
|---|---|
| Fomblin HC/25 | 20% |
| Sorbitol (70% in water) | 39% |
| Texapon N/40 | 2% |
| Vaseline oil | 39% |

Stable emulsion.

EXAMPLE 31

| | |
|---|---|
| Fomblin HC/25 | 8% |
| Glycerol | 27% |
| Diglycerol | 8% |
| Vaselin oil | 55% |
| Texapon N/40 | 2% |

Stable emulsion. Viscosity: 180,000 cps (1 rpm, impeller 4) at 20° C.

EXAMPLE 32

| | |
|---|---|
| Fomblin HC/25 | 5% |
| Glycerol | 30% |
| Amphisol K (*) | 2% |
| Cetiol 868 (**) | 53% |
| Abil K4 (***) | 10% |

(*)potassium cetyl-phosphate produced by Givaudan
(**)octyl stearate produced by Henkel
(***)volatile silicone produced by Tego Cosmetics.

Viscosity: 340,000 cps at 20° C. Stable emulsion.

EXAMPLE 33

| | |
|---|---|
| Fomblin HC/25 | 10% |
| Glycerol | 20% |
| Amphisol K | 3% |
| Cetiol 868 | 63% |
| Abil K4 | 4% |

This preparation was effected in hot conditions by preheating the pre-emulsion to about 50° C. since the viscosity increase which occurs at high oil concentrations makes it difficult to obtain it in cold conditions. Viscosity: 500,000 cps at 20° C. Stable emulsion.

EXAMPLE 34

Examples 34 to 37 illustrate, for comparative purposes, compositions which are not conforming to the present invention.

| | |
|---|---|
| Glycerol | 50% |
| Vaseline oil | 49% |
| Texapon N/40 | 1% |

The emulsion was fully unstable, with quick separation when at rest.

EXAMPLE 35

| | |
|---|---|
| Fomblin HC/25 | 20% |
| Vaseline oil | 79% |
| Texapon N/40 | 1 |

The emulsion was fully unstable, with quick separation of Fomblin HC/25 when at rest.

EXAMPLE 36

| | |
|---|---|
| Fomblin HC/25 | 50% |
| Vaseline oil | 49% |
| Texapon N/40 | 1% |

Stability: as in example 35.

EXAMPLE 37

| | |
|---|---|
| Fomblin HC/25 | 30% |
| Vaseline oil | 67% |
| Arlacel 989 (*) | 3% |

(*)ethoxylated fatty acid produced by I.C.I.
Stability: as in example 35.

EXAMPLE 38

This example illustrates a barrier cream and its preparation:

| A) | glycerine | 20% |
|---|---|---|
| | Fomblin HC/R | 10% |
| | potassium cetyl phosphate | 2% |
| | (Amphisol K produced by Givaudan) | |
| B) | minerla oil | 48% |
| | dimethicone | 20% |

To pre-emulsion A, preheated to about 55° C., phase B was gradually added under stirring. Stirring was then carried on less intensely until room temperature was reached.

The cream viscosity was of 290,000 cps (1 rpm, impeller 6) at 20° C.

EXAMPLE 39

This example illustrates a vitaminic hydrating cream, prepared according to the modalities of example 38:

| A) | glycerine | 30% |
|---|---|---|
| | Fomblin HC/25 | 10% |
| | potassium cetyl phosphate | 2% |
| B) | octyl dodcenaol (Eutanol G produced by Henkel) | 50.5% |
| | cyclomethicone | 5% |
| | (Abil K4 produced by Tego Cosmetics) | |
| | tocopherol acetate | 2% |
| | retinyl palmitate | 0.5% |

The cream viscosity was of 180,000 cps (1 rpm, impeller 6) at 20° C.

EXAMPLE 40

Another vitaminic hydrating cream like the preceding one was prepared, with the exception that 1% of camomile glycolic extract was added.

The presence of this little amount of glycol was sufficient to bring the viscosity from 180,000 cps to 50,000 cps.

EXAMPLE 41

This example relates to a sun-cream prepared as in example 38, with the only exception that phase B was preheated:

| A) | glycerine | 30% |
|---|---|---|
| | Fomblin HC/R | 10% |
| | potassium cetyl phosphate | 2% |
| B) | octyl stearate | 46% |
| | ethyl hexyl p-methoxycinnamate | 5% |
| | (Parisol MCX produced by Gavaudan) | |
| | cyclomethicone | 5% |
| | "Karite butter" | 2% |

The cream viscosity was of 480,000 cps (1 rpm, impeller 6) at 20° C.

What we claim is:

1. Stable emulsions of a first dispersed phase consisting of a perfluoropolyether or perfluoropolyethers having perfluoroalkyl end groups and of a second dispersed phase consisting of one or more fat substances having a melting temperature not higher than 100° C., said two phases being dispersed in a continuous phase consisting of one or more polyhydroxylated compounds selected from glycerol and polyalcohols other than glycerol and saccharides, containing at least three hydroxyl groups, said emulsions having the following weight composition:
   (a) perfluoropolyether or perfluoropolyethers: 1–50% by weight of the emulsion,
   (b) polyhydroxylated compound or compounds: 10–95% by weight of the emulsion,
   (c) fat substance or substances: 10–80% by weight of the emulsion, and
   (d) one or more emulsifiers which are soluble in the polyhydroxylated compound or compounds: 0.1–10% by weight of the emulsion.

2. The stable emulsions according to claim 1, wherein the perfluoropolyether or perfluoropolyethers have a number average molecular weight ranging from 500 to 20,000.

3. The stable emulsions according to claim 1, wherein the polyhydroxylated compounds are selected from diglycerol, triglycerine and tetraglycerine.

4. The stable emulsions according to claim 1, wherein the fat substances are selected from the group consisting of fat alcohols, acids, esters and amides, silicone oils, hydrocarbon oils and fats.

5. The stable emulsions according to claim 1 wherein the emulsifiers are ionic.

6. The stable emulsions according to claim 1, consisting of:
   (a) 5–25% by weight of the emulsion of one or more perfluoropolyethers having perfluoroalkyl end groups, and
   (b) 10–59% by weight of the emulsion of one or more polyhydroxylated compounds, and
   (c) 35–80% by weight of the emulsion of one or more fat substances, and
   (d) 0.3–3% by weight of the emulsion of one or more emulsifiers.

7. The stable emulsions according to claim 6, containing from 10 to 40% by weight of one or more polyhydroxylated compounds.

8. A process for preparing the stable emulsions of claim 1, comprising adding one or more fat substances in the liquid state under stirring to a pre-emulsion of one or more perfluoropolyethers in one or more polyhydroxylated compounds, containing one or more emulsifiers which are soluble in said compounds.

9. The process according to claim 8, wherein when the fat substance is solid at room temperature, the fat substance is added to the pre-emulsion in the molten state or dissolved in a liquid fat substance.

10. Stable emulsions of a first dispersed phase consisting of a perfluoropolyether or perfluoropolyethers having perfluoroalkyl end groups and of a second dispersed phase consisting of one or more fat substances having a melting temperature not higher than 100° C., said two phases being dispersed in a continuous phase consisting of one or more polyhydroxylated compounds selected from glycerol and polyalcohols other than glycerol and saccharides, containing at least three hydroxyl groups, said emulsions having the following weight composition:
   (a) perfluoropolyether or perfluoropolyethers: 1–50% by weight of the emulsion, and
   (b) polyhydroxylated compound or compounds: 10–95% by weight of the emulsion, and
   (c) fat substance or substances: 10–80% by weight of the emulsion, and (d) one or more emulsifiers which are soluble in the polyhydroxylated compound or compounds: 0.1-10% by weight of the emulsion, further comprising up to 20% by weight of the total emulsion of water or of an alcohol wherein components (a), (b), (c) and (d) retain their relative proportions.

11. A preparation for cosmetic and dermatological products, comprising a stable emulsion according to claim 1.

12. The stable emulsions according to claim 1 wherein the polyhydroxylated compound is glycerol.

13. Stable emulsions of a first dispersed phase consisting of a perfluoropolyether or perfluoropolyethers having perfluoroalkyl end groups and of a second dispersed phase consisting of one or more fat substances having a melting temperature not higher than 100° C., said two phases being dispersed in a continuous phase consisting of one or more polyhydroxylated compounds selected from glycerol and polyalcohols other than glycerol and saccharides, containing at least three hydroxyl groups, said emulsions having the following weight composition:

(a) perfluoropolyether or perfluoropolyethers: 1-50% by weight of the emulsion, (b) polyhydroxylated compound or compounds: 10-95% by weight of the emulsion, (C) fat substance or substances: 10-80% by weight of the emulsion, and (d) one or more emulsifiers which are soluble in the polyhydroxylated compound or compounds: 0.1-10% by weight of the emulsion, wherein when the polyhydroxylated compounds are solid, the polyhydroxylated compounds are dissolved in water or in a hydrophilic solvent so that the concentration of polyhydroxylated compound is from 50 to 80% by weight of the solution.

* * * * *